United States Patent [19]

Suthanthiran et al.

[11] Patent Number: 5,163,896
[45] Date of Patent: Nov. 17, 1992

[54] PELLET FOR A RADIOACTIVE SEED

[75] Inventors: Krishnan Suthanthiran, Lorton, Va.; Raj Lakshman, Bethesda, Md.

[73] Assignee: Best Industries, Inc., Springfield, Va.

[21] Appl. No.: 641,898

[22] Filed: Jan. 16, 1991

Related U.S. Application Data

[63] Continuation-in-part of Ser. No. 225,302, Jul. 28, 1988, Pat. No. 4,994,013.

[51] Int. Cl.$^5$ ............................................. A61M 36/00
[52] U.S. Cl. ..................................................... 600/8
[58] Field of Search ............................. 600/1, 3, 7, 8; 424/1.1; 427/5, 6

[56] References Cited

U.S. PATENT DOCUMENTS

| | | |
|---|---|---|
| 821,655 | 5/1906 | Lieber . |
| 1,603,767 | 10/1926 | Harris . |
| 2,269,027 | 1/1942 | Klinghoffer . |
| 2,269,458 | 1/1942 | Kahn . |
| 3,189,581 | 6/1965 | Hart et al. . |
| 3,218,357 | 11/1965 | Roelen et al. . |
| 3,325,459 | 6/1967 | Gander . |
| 3,334,050 | 8/1967 | Grotenhuis et al. . |
| 3,351,049 | 11/1967 | Lawrence . |
| 4,112,213 | 9/1978 | Waldman . |
| 4,228,146 | 10/1980 | Imamura . |
| 4,323,055 | 4/1982 | Kubiatowicz . |
| 4,674,480 | 6/1987 | Lemelson . |
| 4,702,228 | 10/1987 | Russell, Jr. et al. . |

FOREIGN PATENT DOCUMENTS 381407 10/1932 United Kingdom .

OTHER PUBLICATIONS

Technical Innovations and Notes, "Physical Dosimetry of $^{125}$I Seeds of a New Design for Interstitial Implant", vol. 9, pp. 1747-1742.
"Carbon Black", Websters New World Dictionary 2nd Coll. Ed., World Publ. Co. NY, 1970, p. 213.
Encyclopedia of Polymer Science and Technology, vol. 3, John Wiley and Sons, NY, 1965, pp. 367 and 399.
"Ammonium Phosphomolybdate", March Inder, 9th Ed., Merch and Col, Inc., Rahwan, N.J., 1976, p. 585.

*Primary Examiner*—Lee S. Cohen
*Assistant Examiner*—John P. Lacyk
*Attorney, Agent, or Firm*—Parkhurst, Wendel & Rossi

[57] ABSTRACT

A pellet for a radioactive seed, suitable for use in certain medical radiological treatments, including a metallic X-ray detectable marker rod such as tungsten coated with a radioactive-absorbing material, such as a polyamino acid, in a binder wherein a radioactive material is absorbed. Such pellets are encapsulated in a material such as titanium to form an effectively sealed radioactive seed which is useful in certain medical radiological treatments.

47 Claims, 1 Drawing Sheet

PELLET FOR A RADIOACTIVE SEED

This is a continuation-in-part of application Ser. No. 225,302, filed Jul. 28, 1988, now U.S. Pat. No. 4,994,013.

BACKGROUND

The present invention relates to a pellet for a radioactive seed used for medical treatments.

Discrete brachytherapy sources have been known to provide an effective method in the medical treatment of diseased tissues. These discrete sources are implanted into a patient at the site of the diseased tissue. To effectively treat the patient, it is desirable to have such a source which will irradiate the diseased tissue while minimizing damage to nearby healthy tissue. Therefore, it is desirable to have a source which will uniformly irradiate an area being treated with a controlled desired dosage of irradiation. Also desirable is a method of accurately detecting the location of the sources after implantation. The usual construction of such sources comprises a radioactive source which is radiopaque by itself or has an X-ray detectable marker disposed therein.

Radioactive iodine sources used in radiation therapy are known and described, for example, in Lawrence U.S. Pat. No. 3,351,049 and Kubiatowicz U.S. Pat. No. 4,323,055. The radioactive iodine sources described in those patents generally comprise a container for a carrier body of radioactive material and an X-ray marker. The container is generally made from titanium or stainless steel, thereby providing good mechanical strength of the container with minimum absorption of radiation. An X-ray marker is disposed within the container to permit identification by X-ray photographic techniques of the position and number of seeds.

The carrier body disclosed in the Lawrence patent is constructed of a material such as nylon which will chemically or physically capture the selected radioisotope utilized as a source for radiation and maintain a uniform distribution of the isotope in a fixed bed. A marker material is also disposed within the container for X-ray detection.

The patent to Kubiatowicz discloses an X-ray carrier body preferably comprising a silver or silver coated rod. Silver is used because it provides good X-ray detection and because radioactive iodine can be easily attached to the surface thereof by chemical or electroplating processes. However, the interaction of the X-rays from I-125 with the silver produces still lower energy radiations characteristic of silver thus degrading the total I-125 spectrum from the source.

However, it will be appreciated that the prior art fails to recognize a convenient and advantageous method for providing a radioactive iodine source which provides maximum radioactive absorption while being X-ray detectable along its longitudinal axis, and without distorting the characteristic X-ray spectrum of I-125. Also, the prior art fails to recognize a method for easily manufacturing quantities of radioactive sources having a desired controlled radioactivity.

SUMMARY OF THE INVENTION

Accordingly, it is an object of the present invention to provide a new and useful radioactive pellet which overcomes the shortcomings of the prior art.

It is an object of the present invention to provide a radioactive pellet capable of providing desired uniform distribution of radioactivity.

It is another object of the present invention to provide a process for coating a radioactive-absorbing material onto a metal substrate.

It is an object of the present invention to provide a radioactive pellet wherein radioactive material is absorbed by a coating of radioactive-absorbing material in a binder.

It is a further object of the present invention to provide a radioactive pellet wherein radioactive material is absorbed by a flexible carrier film containing a radioactive-absorbing material, provided on a metal substrate.

It is still a further object of the present invention to provide a balanced coating of radioactive-absorbing material, such as a polyamino acid, and binder to maximize absorption of radioactive material.

The foregoing objects and others are achieved by providing a radioactive absorption composition comprising a metallic X-ray detectable marker coated with radioactive-absorbing material in a binder wherein radioactive material such as radioactive iodine is absorbed chemically (and physically) by the radioactive-absorbing material, such as a polyamino acid, thereby providing a balance of radioactive-absorbing material and binder to maximize radioactive absorption. The X-ray marker preferably comprises tungsten.

BRIEF DESCRIPTION OF THE DRAWINGS

For a better understanding of the structure, advantages and further features of the radioactive pellets of the present invention, reference is made to the accompanying drawings of various embodiments thereof, wherein.

DETAILED DESCRIPTION OF THE INVENTION

Figure 1:
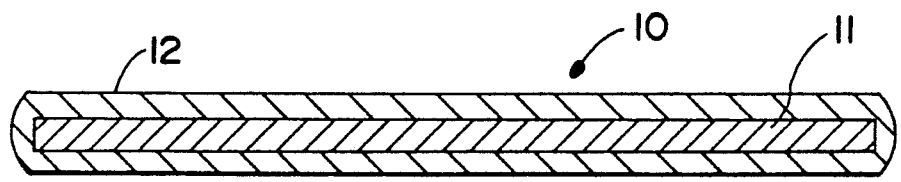
FIG. 1 is a partially schematic cross-sectional view showing a preferred embodiment of the internal structure of the radioactive pellets of the present invention.

A preferred embodiment of the internal structure of the advantageous radioactive pellet of the present invention is illustrated in FIG. 1. The radioactive pellet 10 comprises a metal substrate 11 having a coating 12 uniformly and completely provided thereon. The metal substrate preferably comprises an elongate rod of tungsten or a tungsten alloy. Tungsten is the material of choice because it has mechanical strength which provides a straight substrate on which to coat the radioactive-absorbing material and binder. An elongate metal rod made of tungsten imparts stability to the resulting pellet. Furthermore, tungsten is easily detectable by X-ray techniques, and therefore serves as a marker for the radioactive absorption composition. Other materials such as stainless steel or tin may be utilized as the marker, however, tungsten is the most preferred material.

The tungsten rod or marker 11 is coated with radioactive-absorbing material in a binder material. By radioactive absorbing material we mean any material which will absorb (chemically and/or physically) another fluid radioactive material. Such radioactive-absorbing materials may include carbon, activated carbon or charcoal, and ion-exchange resins such as sulfonated polystyrene resins which are available from the Dow Chemical Co. under the trade-name DOWEX, methylene-sulfuric phenolic resins, phosphoric polystyrene resins, polystyrene resins containing quaternary ammonium groups, immodiacetic polystyrene resins, and polystyrene resins containing polyamine groups. Other materials may also be used.

A preferred material for the radioactive-absorbing material is a polyamino acid. The polyamino acid material may be combined with a binder and applied to the marker 11 before or after impregnation with a radioactive material. Such polyamino acids can be formed from polyamino acids which are capable of chemically binding radioactive substituents. The radioactive substituent to be chemically bound by the polyamino acid is preferably employed through the use of $^{125}I$ sodium iodide with a specific activity of about 17.4 Ci/mg. In particular, an aromatic polyamino acid such as polytyrosine (which is commercially available in powder form) can be labeled with $^{125}I$ at the 3' and 4' positions of the aromatic ring of the tyrosine molecules of the polypeptide chain.

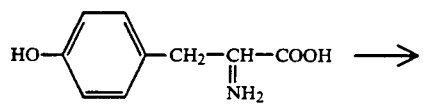

Tyrosine

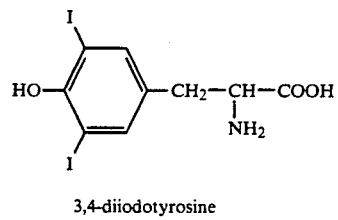

3,4-diiodotyrosine

Theoretically, each tyrosine residue is capable of taking up two atoms of iodine. A polytyrosine of molecular weight of about 100,000 has about 553 tyrosine residues. Thus, one mole of polytyrosine can bind about 1,105 iodine atoms. In gravimetric terms, each milligram of polytyrosine can thus bind about 8-10 Ci of $^{125}I$. Therefore, it is evident that a small quantity of polytyrosine is capable of tightly chemically binding an enormous amount of $^{125}I$.

Preferably, poly-D-tyrosine labeled with $^{125}I$ is employed as the radioactive-absorbing material/radioactive material combination. The advantages of utilizing the D isomer of polytyrosine are particularly evident should polytyrosine enter the body. Free $^{125}I$ is known to be readily taken up by the body in the thyroid gland. Poly-D-tyrosine, being the unnatural isomer for higher organisms including man, cannot be broken down by the body. Thus, the $^{125}I$ will remain effectively chemically bound to the poly-D-tyrosine, and not be taken up by the thyroid gland. It is well known that free iodine, including the radioactive form thereof, has a great tendency to accumulate in the thyroid when iodide is free to move within the body.

It is evident that polyamino acids other than polytyrosine, as well as radioisotopes other than $^{125}I$, may be used in the present invention. A useful radioisotope must be capable of binding with available sites on the polyamino acid. For example, $^{14}C$ may be incorporated into the epsilon amino group of lysine by reductive methylatin with $^{14}C$ label on the lysine molecule. Other radioisotopes such as $^{32}P$ can also be incorporated into polynucleotides (polyamino acids). Some polynucleotides which can be labeled with $^{32}P$ include polyadenylic acid, polyguanylic acid, polythymidylic acid, polycytidylic acid and the like.

It will be appreciated that other large molecules including polymers can be selected having a varying number of available binding sites, thereby permitting the total radioactivity of the final radioactive source to vary.

When the polyamino acid is to be applied to the marker/substrate and subsequently impregnated with radioactive material, it is necessary to combine the acid (in powder form) with an appropriate binder material.

Such a binder material is selected which can readily bond to the substrate and absorb radioactive material without disintegrating or breaking away from the substrate. The binder is preferably water insoluble, so that aqueous solutions of radioactive materials may be used to impregnate the radioactive material into the radioactive-absorbing material. It is believed that the chain length of polymeric binder materials should be long enough to bind the material to the substrate, but also permit the radioactive material to be absorbed physically therein. As explained above, if a polyamino acid, such as polytyrosine, is used as the radioactive-absorbing material, the radioactive material will bind chemically with the polytyrosine. The radioactive material thus will be both chemically and physically bound to the radioactive-absorbing material.

Where water-insoluble binders are used, the binder material should have a sufficient number of hydrophilic groups to permit absorption of the radioactive material. Such water insoluble binder materials include cellulose esters such as cellulose acetate, cellulose propionate, cellulose butyrate, and the like. Depending upon the acyl content and hydroxyl content of the cellulose ester, the binding and water absorbing properties of the cellulose ester can be varied. For example, a cellulose acetate presently commercially available has an acetyl content of about 45% (i.e., the percentage of hydroxyl groups in the cellulose which are esterified). When a binder/radioactive absorbing material composition contains about 30% by weight of such a cellulose ester, that binder/radioactive absorbing material layer provides excellent binding and water absorbing properties. Other water insoluble materials such as hydrogenated rosin esters, alkyd resins, silicone resins, polystyrene-olefin copolymers, polystyrene-vinyl toluene copolymers, phenylmethyl silicone resin, phenolformaldehyde resins, and the like may be used. Where such materials may more completely seal the radioactive absorbing material bound therein, that radioactive material may be more preferably primarily located in a substantially discrete layer at or near the outer surface of the layer of binder material.

It will also be appreciated that where the desired radioactive materials are soluble or suspendable in organic solvents, the binder material may be water-soluble but insoluble in such organic solvents, again to preserve the integrity of the binder layer on the substrate during application of the radioactive material. Such water soluble binder materials may include readily available water soluble materials like disaccharides such as sucrose, maltose and the like, polysaccharide such as starch, glycogen and the like, inorganic compositions such as plaster of Paris, calcium sulfate and the like.

Figure 3:
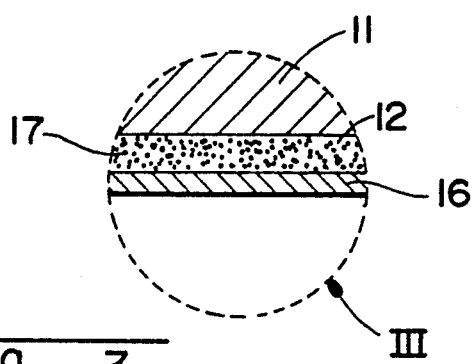
FIG. 3 is a partially schematic enlarged view of a portion of the cross-sectional view of FIG. 2.

As better illustrated in FIG. 3, the radioactive-absorbing material 17 is typically particulate (particle size ranging from about 1.0 micron to about 100 microns) and is dispersed throughout the layer 12 of the binder material. However, the radioactive-absorbing material may, in various embodiments, be located in a more discrete layer at or near the outer surface of the binder material layer 12.

The metallic radiopaque marker rods are coated with binder and radioactive absorbing material, such as polytyrosine and cellulose acetate, in an airborne tumbling process which resembles a fluidized bed system. In one such system tungsten rods are fluidized by blowing a suspension of polytyrosine particles in cellulose acetate dissolved in acetone upwardly through a bed of the rods, thereby substantially uniformly coating the rods with a polytyrosine in cellulose acetate matrix.

It is desirable to have a balance between the radioactive-absorbing material and binder such that radioactive absorption is maximized. In other words, it is desirable to have a sufficient quantity of binder to hold the radioactive-absorbing material on the substrate while having a large amount of the latter material available for absorption of radioactive material. It has been found that about 25% by weight of radioactive absorbing material, such as polytyrosine, with about 75% by weight of binder, such as cellulose acetate, provides a good balance. While the ratio of about 25% radioactive-absorbing material to about 75% binder is preferred, such matrices may be suitable with binder present in amounts in the range of from about 10 to about 90% of the total binder/absorptive material matrix. It also is possible to use composite mixtures of radioactive-absorbing materials, such as polytyrosine powder mixed with a carbon powder.

In another embodiment of the invention a polyamino acid, such as polytyrosine, is labeled with radioactive material in a solution, and the resultant radio-labeled polyamino acid is coated onto or dispersed in a flexible carrier film. The impregnated flexible carrier film is then adhered to the marker/substrate via a suitable adhesive. A thin coating can be easily coated uniformly onto or dispersed in the flexible carrier film giving a desired amount of radioactivity per unit area of the flexible carrier film. Depending upon the amount of radiation exposure desired from the film product, more or less radioactive material can be incorporated onto the flexible carrier film. Typically, the flexible carrier film is made of a material which can selectively trap the radioactive material while impurities are not retained.

A membrane filter having uniform pore size may be utilized as the flexible carrier film. The membrane filter is chosen such that when labeled polyamino acid in solution is passed through the membrane filter, the polyamino acid is trapped while impurities are allowed to pass therethrough. The pore size in the membrane filter will typically range from about 0.1 microns to about 10 microns so that compounds of molecular weight larger than about 10,000 are trapped while impurities having a molecular weight less than about 10,000 are allowed to pass. In other words, a membrane filter is selected having a pore size which will not allow the radioactively labeled polymer molecules of molecular weight more than 10,000 to pass, but will allow smaller molecules such as free $^{125}I$ sodium iodide or other reactants to pass uninhibited. For example, when preparing radio-labeled polyamino acid in solution, the solution may contain labeled polyamino acid as well as unreacted free radioisotopes and other reactants. By selecting a membrane filter having a pore size which selectively retains the labeled polyamino acid, the unreacted free radioisotopes and other reactants can be removed by thoroughly washing the filter with water. The radiolabeled polyamino acid will be selectively retained on the filter. Therefore, the particular labeled polyamino acid can be uniformly coated on the filter as a thin coating.

The pore size of the filter utilized will depend on the molecular weight or size of the labeled polyamino acid. Typically, a pore size of about 0.45 microns is adequate to trap the polyamino acid while allowing impurities to pass. Other suitable pore sizes can range from about 0.1 microns to about 1 micron. Examples of such materials for the membrane filter include polyvinyl chloride, polytetrafluoroethylene, polysulfones, cellulose esters, nylon, Dacron, polypropylene and the like.

The flexible carrier film can range from about 20 to about 1000 microns thick, and is typically about 125 microns thick, allowing it to be easily cut into any desired dimension or shape depending on the particular application. Preferably the film is in the form of a strip having a width substantially equal to the length of the marker/substrate. The film is them wound around the marker as many times as necessary to achieve a desired radioactivity level.

The radioactive material to be absorbed into the matrix of the pellet's internal structure, or mixed with a polyamino acid and deposited on the flexible carrier film is preferably I-125. However, other radioactive materials such as Pd-103, Cs-131, Cs-134, Cs-137, Ag-111, U-235, Au-198, P-32 and C-14, as well as isotopes of rubidium, calcium, barium, scandium, titanium, chromium, manganese, iron, cobalt, nickel, copper, zinc, yttrium, zirconium, indium, cadmium, the rare earths, mercury, lead, americium and neptunium may be used in various applications. The radioactive materials are preferably in fluid or liquid form to facilitate impregnation of the radioactive-absorbing material into the matrix. For example, an aqueous solution of I-125 sodium iodide is preferably used to impregnate a polytyrosine/cellulose acetate coated tungsten rod.

The internal pellets and encapsulated seeds of the present invention are quite small. The metallic rod substrates are typically of a length in the range of about 1 mm to about 10 mm, and of a diameter in the range of about 0.1 mm to about 1.0 mm. While circular cross-sectioned rods are preferred, rods having other cross sections may be used. The coating of radioactive-absorbing material and binder or flexible carrier film is typically of a thickness in the range of about 0.01 mm to about 1.0 mm, and preferably that coating or film substantially uniformly coats the entire rod, including its ends, as illustrated in FIG. 1. Thus the diameter of the coated internal pellet is in the range of about 0.05 mm to about 3.0 mm. The external capsule which effectively seals the internal pellet to form a useful radioactive seed is typically of a size in the range of about 1.5 mm to about 15 mm in length, with a diameter in the range of about 0.3 to about 4.0 mm. Depending upon the materials used in the pellet and capsule, the total thickness of the capsule wall may be in the range of about 0.05 mm to about 1.0 mm.

For example, substrates having dimensions of about 4 mm in length and about 0.25 mm in diameter are coated with a layer of polyamino acid and binder of approximately 0.1 mm in thickness. The tungsten markers coated by the polyamino acid and binder have final dimensions of about 0.45 mm in diameter and about 4.5 mm in length. Each pellet is thus capable of absorbing I-125 in amounts in excess of about 50 mCi.

In order to obtain the desired radioactivity, the polyamino acid-coated pellets are loaded with a solution of one of the suitable radioactive materials, such as I-125 NaI, at a desired concentration, such as 1000 mCi/ml. Each pellet is capable of absorbing a certain amount of liquid. Therefore, only a certain amount of radioactive material can be loaded at one time. If more radioactive material is desired to be absorbed onto the coating, multiple cycles of loading and drying of the pellet may be used. If a flexible carrier film is used, the film may be wound more than once around the marker. During these cycles of loading and drying, the pellets are allowed to absorb their maximum amount of solution of the radioactive material. Then the pellets are dried briefly, typically with a high intensity lamp. The process of loading and drying is repeated until the desired amount of radioactivity is obtained. Utilizing this method, large batches of radioactive pellets can be manufactured.

While the amount of radioactivity present in each pellet may vary in a range of about 0.1 to about 2000 mCi, most pellets contain about 0.3 to about 100 mCi. Also, the amount of radioactivity per pellet, expressed in mCi, varies depending upon the particular radioisotope being used and the desired application for the pellets.

After the pellets have been loaded with the desired amount of radioactive material, each pellet is encapsulated. Typically, encapsulation is in titanium capsules which effectively seal the pellet. The pellet may be encapsulated in a container made of material other than titanium, provided that the container material does not substantially inhibit irradiation from the seed, and provided that the material is resistant to corrosion by body fluids. Other materials useful for the capsule or container may include stainless steel, platinum, gold, nickel alloy, organic plastic materials such as nylon, silicon, rubber, polyester resin, and fluorinated hydrocarbons, or aluminum and aluminum alloys sealed with an inert overcoating. After the pellets are encapsulated, the actual activity of each seed is monitored by dosimetry. The encapsulated seed can then be implanted into the desired treatment area.

Figure 2:
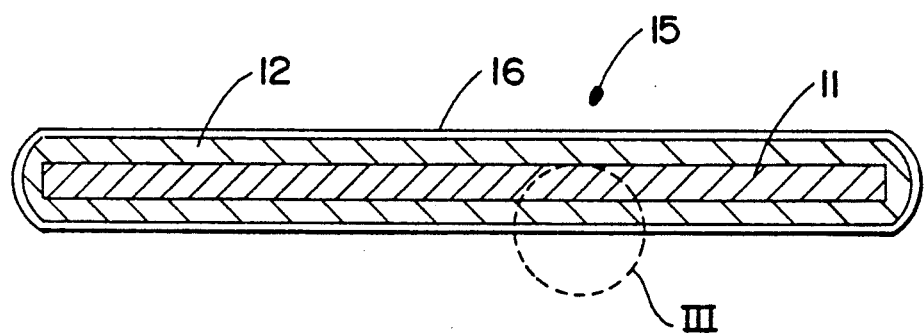
FIG. 2 is a partially schematic longitudinal cross-sectional view of a preferred embodiment of the radioactive seeds of the present invention.

A preferred embodiment of the radioactive seeds 15 of the present invention is illustrated in FIG. 2. The seed shown in FIG. 2 is substantially the same as the pellet disclosed in FIG. 1 with the addition that a tubular envelope or capsule 15 is provided around the polyamino acid-coated internal pellet structure. In this embodiment, the tungsten rod is coated with polytyrosine, or other suitable radioactive-absorbing material, and binder, and is further loaded with a radioactive isotope as described above. The pellet internal structure thus obtained is sealed or substantially sealed in a tubular envelope or capsule which is preferably made of titanium. In this embodiment, the coating of polytyrosine is of uniform thickness and density, and therefore the irradiation emanating therefrom will be substantially uniform. As with the first preferred embodiment, the pellet thus constituted is loaded with the desired radioactivity, encapsulated preferably by a titanium container, and the resulting radiation of the seed is monitored by dosimetry. Such capsules and encapsulating techniques are further discussed in our copending application Ser. No. Jan. 2, 1990, the entire disclosure of Which is hereby incorporated by reference herein.

The methods of making and loading the radioactive pellets of the present invention are further illustrated by reference to the following examples.

EXAMPLE 1

Tungsten marker rods about 4 mm in length and about 0.25 mm in diameter are uniformly coated with about 25% by weight polytyrosine and about 75% by weight cellulose acetate binder, said cellulose acetate having an acetyl content of about 45%, to form a pellet about 0.45 mm in diameter and about 4.5 mm in length. Each pellet is allowed to absorb about 1.0 μl of I-125 NaI solution with a concentration of about 1000 mCi/ml. When all of the solution is completely absorbed by each pellet by capillary action and bound chemically to the polytyrosine material, the pellets are dried under a high intensity lamp. The process of loading and drying is repeated several times depending upon the amount of radioactivity desired in each pellet. Each pellet is allowed to react with 1 μl of chloramine T solution (75 mg/1ml) for 30 seconds at room temperature followed by the addition of 1 μl of sodium metabisulfite solution (500 mg/ml) to stop the reaction. The pellet is then dried under high intensity lamp. Each pellet is then encapsulated in a titanium capsule. The surfaces of the capsules are wiped clean until the removable contamination is reduced to less than 0.005 μCi. The actual radio activity of the final product is measured using an appropriately calibrated ionization chamber. The final dimensions of the encapsulated seeds are about 0.6 mm in diameter by about 5.0 mm in length.

EXAMPLE 2

A tungsten marker substrate having dimensions of about 4 mm in length and about 0.25 mm in diameter is coated with a layer of polytyrosine and cellulose acetate binder, as in Example 1, approximately 0.1 mm in thickness. The tungsten markers coated by the polytyrosine and binder have final dimensions of about 0.45 mm in diameter and about 4.5 mm in length. The polytyrosine-coated pellets are loaded with a solution of I-125 NaI, at a concentration of 500 mCi/ml. Each pellet is capable of absorbing approximately 1 μl of liquid. Approximately 0.5 mCi of I-125 can be loaded at one time. If more radioactive material is desired to be absorbed onto the polytyrosine coating, multiple cycles of loading and drying of the pellet may be used. With a solution concentration of about 500 mCi/ml I-125, each pellet typically goes through two cycles of loading and drying for each mCi of I-125 loaded. During these cycles of loading and drying, the pellets are allowed to absorb the maximum amount of I-125 solution. Then the pellets are dried briefly, typically with a high intensity lamp. The process of loading and drying is repeated until the desired amount of radioactivity is obtained. The radioactivity of each seed so produced is measured using an appropriately calibrated ionization chamber.

EXAMPLE 3

A solution (about 50 μ1) of poly-D-tyrosine (Sigma Chemical Co., St. Louis, Mo.), approximately 2 mg/ml in 0.1 M NaOH is placed in a Beckman microfuge tube to which about 50 μl of 1 N HCl is added followed by the addition of about 50 μl of 0.2 M borate buffer, pH 7.9. Iodination is carried out by adding about 2 μl of career-free $^{125}$I-sodium iodide (Syntechem Co., N.Y., N.Y., 0.5 Ci/ml) followed by the addition of about 50 μl of chloroamine-T solution, 30 mg/ml H$_2$O, (Eastman Kodak Ltd., Rochester, N.Y.). The mixture is allowed to react for 30 seconds when about 50 μl of sodium metabisulfite 10 mg/ml H$_2$O (Fisher Scientific Co., Columbia, Md.) is added to stop the reaction. The final reaction mixture is filtered under reduced pressure through a hydrophilic Durapore filter about 175 microns thick, being about 0.45 micron pore size (Millipore Corporation, Bedford, Mass.). The filter then is washed thoroughly with water to remove unreacted free $^{125}$I sodium iodide and all other reactants. The $^{125}$I labeled polytyrosine does not pass completely through the pores of the filter and is selectively retained on the filter. Thus, $^{125}$I is uniformly coated on the filter as a thin film giving a desired amount of radioactivity. The filter is air dried and then adhered to a tungsten marker rod via a suitable adhesive. Each pellet then is encapsulated in a titanium capsule as in Example 1 above.

While the foregoing descriptions of the advantageous radioactive pellets and seeds of the present invention have described various embodiments thereof, it will be appreciated by those skilled in the art that various modifications can be made in such radioactive pellets and seeds without departing from the scope or spirit of the invention as stated in the following claims.

What is claimed is:

1. A pellet for a radioactive seed for use in radiation therapy, comprising a metallic substrate uniformly and completely coated with a radioactive-absorbing material comprising polyamino acids.

2. The pellet of claim 1, wherein said polyamino acids include at least one acid selected from the group consisting of polytyrosine, polyadenylic acid, polyguanylic acid, polythymidylic acid, and polycytidylic acid.

3. The pellet of claim 1, wherein said polyamino acid consists of polytyrosine.

4. The pellet of claim 3, wherein said polytyrosine is poly-D-tyrosine.

5. The pellet of claim 1, wherein said radioactive-absorbing material further comprises at least one material selected from the group consisting of carbon, activated carbon and charcoal.

6. The pellet of claim 1, wherein said radioactive-absorbing material is mixed with a binder material, and then coated on said metallic rod substrate.

7. The pellet of claim 6, wherein said binder material is water-insoluble.

8. The pellet of claim 6, wherein said binder material is a cellulose ester.

9. The pellet of claim 6, wherein said binder material comprises cellulose acetate.

10. The pellet of claim 6, wherein said binder material is insoluble in organic solvents.

11. The pellet of claim 6, wherein said coating of binder material has a thickness in the range of about 0.01 mm to about 1.0 mm.

12. The pellet of claim 6, wherein said radioactive absorbing material is particulate and dispersed throughout the binder material.

13. The pellet of claim 6, wherein said radioactive absorbing material is particulate and is located primarily in a discrete layer at or near an outer surface of the binder material.

14. The pellet of claim 6, wherein said radioactive-absorbing material comprises an amount in the range of about 10% to about 90% by weight of the total binder/radioactive-absorbing material.

15. The pellet of claim 14, wherein said binder material comprises about 75% by weight and the radioactive-absorbing material comprises about 25% by weight of the total binder/radioactive-absorbing material.

16. The pellet of claim 1, wherein said radioactive-absorbing material is coated onto or dispersed in a flexible carrier film, and then the film is adhered to said metallic substrate.

17. The pellet of claim 16, wherein said radioactive-absorbing material further comprises at least one material selected from the group consisting of carbon, activated carbon and charcoal.

18. The pellet of claim 16, wherein said flexible carrier film comprises a material selected from the group consisting of polyvinyl chloride, polytetrafluoroethylene, cellulose esters and polysulfones.

19. The pellet of claim 16, wherein said flexible carrier film is a membrane filter.

20. The pellet of claim 19, wherein said membrane filter has a pore size sufficiently small to trap radioactive material thereon.

21. The pellet of claim 20, wherein said pore size ranges from about 0.1 microns to about 10.0 microns.

22. The radioactive pellet of claim 21, wherein said pore size is about 0.45 microns.

23. The pellet of claim 16, wherein said flexible carrier film is from about 20 to about 10.0 microns thick.

24. The pellet of claim 23, wherein said flexible carrier film is about 125 microns thick.

25. The pellet of claim 1, wherein said metallic substrate comprises a material selected from the group consisting of tungsten, stainless steel, tin, or alloys thereof.

26. The pellet of claim 1, wherein said metallic rod substrate comprises tungsten or an alloy thereof.

27. The pellet of claim 1, wherein said metallic substrate is rod-shaped and has a length in the range of about 1 mm to about 10 mm and a diameter in the range of about 0.1 mm to about 1.0 mm.

28. The pellet of claim 1, wherein said metallic substrate has a circular cross-section.

29. The pellet of claim 1, wherein said radioactive-absorbing material further comprises an ion exchange resin.

30. The pellet of claim 29, wherein said ion-exchange resin further comprises at least one material selected from the group consisting of sulfonated polystyrene resins, methylene-sulfonic phenolic resins, phosphoric polystyrene resins, polystyrene resins containing quaternary ammonium groups, pyridinium polystyrene resins, epoxy-polyamine resins containing tertiary and quaternary ammonium groups, iminodiacetic polystyrene resins, and plystyrene resins containing polyamine groups.

31. The pellet of claim 1, wherein said radioactive-absorbing material is particulate and of a particle size in the range of about 1.0 micron to about 100.0 microns.

32. The pellet of claim 1, having radioactive material absorbed in the radioactive absorbing material, said radioactive material being selected from the group consisting of I-125, Pd-103, Cs-131, Cs-134, Cs-1378, Ag-111, U-235, Au-198, P-32 and C-14, as well as isotopes of rubidium, calcium, barium, scandium, titanium, chromium, manganese, iron, cobalt, nickel, copper, zinc, yttrium, zirconium, indium, cadmium, the rare earths, mercury, lead, americium and neptunium.

33. The pellet of claim 32, wherein said radioactive material is absorbed chemically by said radioactive-absorbing material.

34. The pellet of claim 32, wherein said radioactive material therein is I-125.

35. A radioactive seed comprising the pellet of claim 1, having radioactive material, absorbed in the radioactive absorbing material, further including an external capsule covering the exterior of the radioactive-absorbing material and substantially sealing the pellet within the capsule.

36. The seed of claim 35, wherein said capsule comprises at least one material selected from the group consisting of titanium, stainless steel, platinum, gold, nickel alloys, nylon, silicon, rubber, polyester resin, chlorinated hydrocarbon resins, aluminum, and aluminum alloys.

37. The seed of claim 35, wherein said capsule comprises titanium.

38. The seed of claim 35, wherein a wall thickness of said capsule is in a range of about 0.05 mm to about 1.0 mm.

39. The seed of claim 35, wherein said capsule is of a size in the range of about 1.5 mm to about 15 mm in length, and about 0.3 mm to about 4.0 mm in diameter.

40. The seed of claim 35, wherein an amount of radioactivity present therein is in the range of about 0.1 about 2000 mCi.

41. The radioactive seed of claim 35, wherein an amount of radioactivity therein is in the range of about 0.3 to about 100 mCi.

42. The pellet of claim 35, wherein said capsule comprises organic plastic materials.

43. The seed of claim 1, wherein said metallic substrate consists of a metallic rod substrate.

44. A pellet for a radioactive seed for use in radiation therapy, comprising a metallic substrate coated with a radioactive-absorbing material comprising polyamino acids which chemically react with radioactive substituents to form a stable chemical compound.

45. A pellet for a radioactive seed for use in radiation therapy, comprising a radioactive-absorbing material comprising polyamino acids which chemically react with radioactive substituents to form a stable chemical compound.

46. The pellet of claim 45, wherein said polyamino acids consist of polytyrosine.

47. The pellet of claim 46, wherein said polytyrosine is poly-D-tyrosine.

* * * * *